(12) United States Patent
Ishihara et al.

(10) Patent No.: US 9,146,239 B2
(45) Date of Patent: Sep. 29, 2015

(54) METHOD OF JUDGING RISK OF CANCER RECURRENCE AND COMPUTER PROGRAM

(71) Applicant: SYSMEX CORPORATION, Kobe-shi, Hyogo (JP)

(72) Inventors: Hideki Ishihara, Miki (JP); Tomoko Matsushima, Kobe (JP); Satoshi Nakayama, Toda (JP); Manfred Schmitt, Munich (DE); Marion Kiechle, Munich (DE); Rupert Langer, Bern (CH); Ulrike Schwarz-Boeger, Munich (DE)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 13/682,377

(22) Filed: Nov. 20, 2012

(65) Prior Publication Data

US 2013/0323748 A1    Dec. 5, 2013

(30) Foreign Application Priority Data

Nov. 29, 2011 (JP) ................................. 2011-260446

(51) Int. Cl.
  *G01N 33/48* (2006.01)
  *G01N 33/574* (2006.01)
  *G06F 19/00* (2011.01)
  *G06F 19/20* (2011.01)

(52) U.S. Cl.
  CPC .... *G01N 33/57496* (2013.01); *G01N 33/57492* (2013.01); *G06F 19/3437* (2013.01); *G06F 19/20* (2013.01)

(58) Field of Classification Search
  CPC .......................................................... G06F 19/20
  USPC .............................................................. 702/19
  See application file for complete search history.

(56) References Cited

U.S. PATENT DOCUMENTS

2007/0231837 A1    10/2007    Ishihara et al.
2009/0246809 A1    10/2009    Shibayama et al.

OTHER PUBLICATIONS

Van Nes et al. "Validation of the Prognostic Value of Cyclin-Dependent Kinase (CDK)—Based Risk in Caucasian Breast Cancer Patients" (2009) vol. 100, pp. 494-500.*
Duffy, Michael "Urokinase Plasminogen Activator and Its Inhibitor PAI—as Prognostic Markers in Breast Cancer: From Pilot to Level I Evidence Studes" Clinical Chemistry (2002) vol. 48, No. 8, pp. 1194-1197.*
Nadia Harbeck, et al., "Clinical Relevance of Invasion Factors Urokinase-Type Plasminogen Activator and Plasminogen Activator Inhibitor Type 1 for Individualized Therapy Decisions in Primary Breast Cancer Is Greatest When Used in Combination", Journal of Clinical Oncology, Feb. 15, 2002, p. 1000-1007, vol. 20, No. 4.

\* cited by examiner

*Primary Examiner* — Jerry Lin
(74) *Attorney, Agent, or Firm* — Sughrue Mion, PLLC

(57) ABSTRACT

There is provided a method of judging a risk of cancer recurrence based on the activity value and expression level of the first CDK, the activity value and expression level of the second CDK, and the expression levels of uPA and PAI-1 and a computer program.

15 Claims, 5 Drawing Sheets

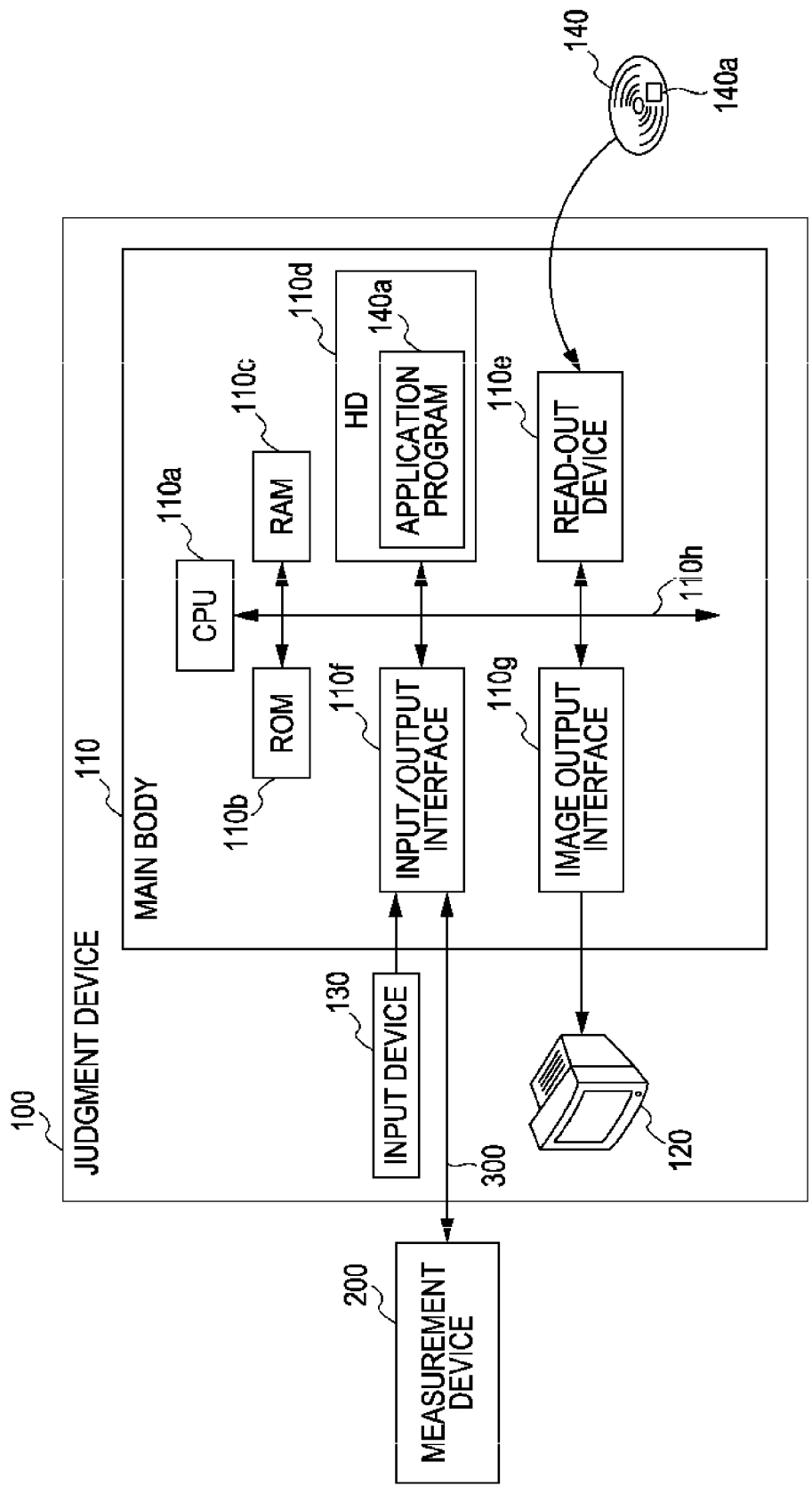

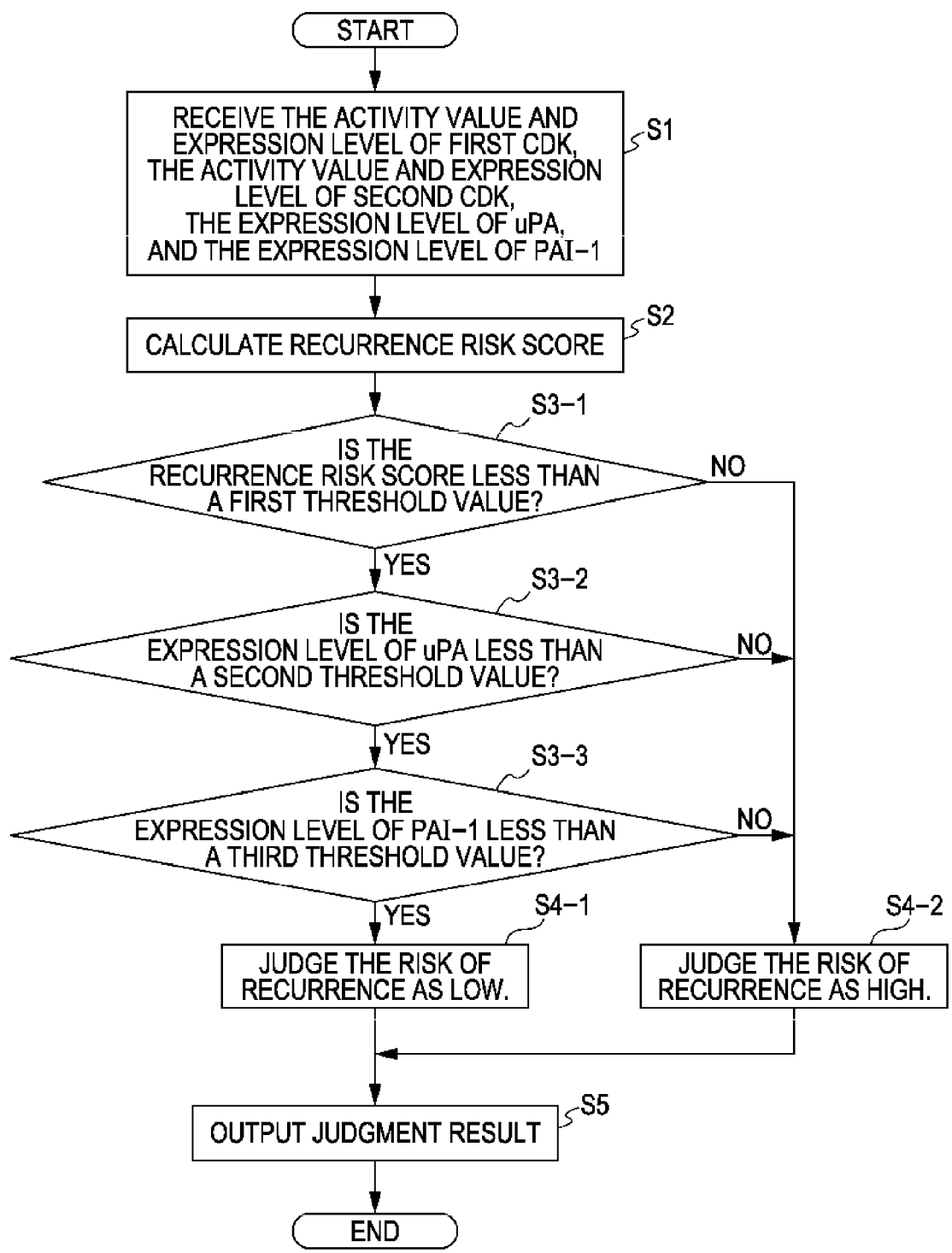

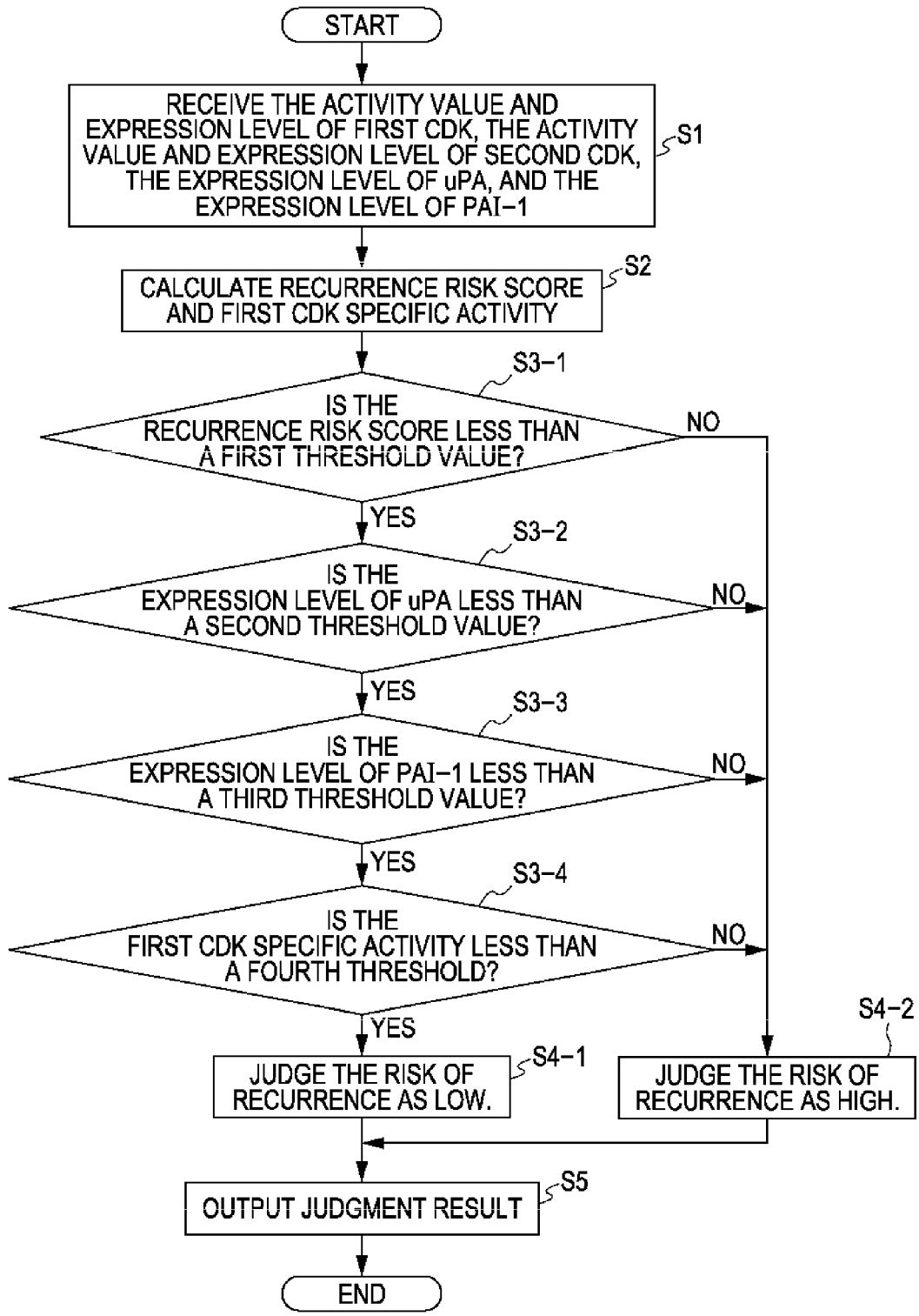

CONVENTIONAL METHOD 1

CONVENTIONAL METHOD 2

PRESENT INVENTION

METHOD OF JUDGING RISK OF CANCER RECURRENCE AND COMPUTER PROGRAM

FIELD OF THE INVENTION

The present invention relates to a method of judging a risk of cancer recurrence and a computer program to allow a computer to execute the method.

BACKGROUND

In the cancer treatment field, it is known that even if a primary carcinoma is treated by surgical resection, radiotherapy, chemotherapy or the like, cancer will recur at a certain rate. Further, it is known that many cases with recurrent cancer have a high degree of malignancy. Actually, the number of patients who will die due to cancer recurrence is higher than that of patients who will die due to the primary carcinoma. That is, the cancer recurrence is an important problem which determines a patient's prognosis. Hence, a process of judging a risk of cancer recurrence in patients whose primary carcinoma has been treated by surgery is very useful in determining a course of treatment after treatment as to the necessity of adjuvant chemotherapy.

Some factors for judging a risk of cancer recurrence are known in the art. Examples of the factors include age of patient, size of tumor, stage of progression, tumor tissue, nuclear grade classification, and presence of lymph node metastasis. Recently, many biomarkers according to the type of cancer have been identified. These biomarkers are used for the discovery of cancer and prognostic expectation. For example, as for breast cancer, hormone receptors such as estrogen receptors and receptor tyrosine kinases such as Her2 have attracted attention as biomarkers. Harbeck N. et al. have reported that a risk of breast cancer recurrence can be judged based on the expression levels of a urokinase plasminogen activator (uPA) and a plasminogen activator inhibitor 1 (PAI-1) (Harbeck N. et al., J. Clin. Oncol., vol. 20, No. 4, pp. 1000-1007 (2002) "Clinical Relevance of Invasion Factors Urokinase-Type Plasminogen Activator and Plasminogen Activator Inhibitor Type 1 for Individualized Therapy Decisions in Primary Breast Cancer Is Greatest When Used in Combination").

The present inventors have disclosed methods of judging a degree of malignancy of cancer cells and a risk of cancer recurrence based on the expression levels and activity values of two types of cycline-dependent-kinases (CDK) (US2007/0231837 and US2009/0246809).

SUMMARY OF THE INVENTION

The scope of the present invention is defined solely by the appended claims, and is not affected to any degree by the statements within this summary.

Adjuvant chemotherapy which is given to patients to prevent cancer recurrence becomes a physical, psychological, and economical burden on patients. Accordingly, there has been a request to avoid such therapy. Under such a request, in order to provide an index for judging that adjuvant chemotherapy is not given after treatment of the primary carcinoma to doctors, there is a need for a method of judging a risk of recurrence to have very high accuracy.

Then, an objective of the present invention is to provide a method which can accurately judge a risk of cancer recurrence. Another objective of the present invention is to a computer program to allow a computer to execute the method.

Surprisingly, the present inventors have found that when the risk of cancer recurrence is judged based on the expression levels and activity values of two types of cycline-dependent-kinases (CDK) and the expression levels of a urokinase plasminogen activator (uPA) and a plasminogen activator inhibitor 1 (PAI-1) in specimens extracted from cancer patients, the judgment accuracy becomes significantly higher than that of the conventional method. Thus, they have completed the present invention.

That is, according to the present invention, there is provided a method of judging a risk of cancer recurrence including step of: acquiring an activity value and expression level of a first CDK, an activity value and expression level of a second CDK, an expression level of uPA, and an expression level of PAI-1 from biological samples extracted from cancer patients; and judging a risk of cancer recurrence based on the acquired activity value and expression level of the first CDK, the activity value and expression level of the second CDK, the expression level of uPA, and the expression level of PAI-1.

According to the present invention, there is provided a computer program to allow a computer to execute the steps of receiving an activity value and expression level of a first CDK acquired from biological samples extracted from cancer patients, an activity value and expression level of a second CDK, an expression level of uPA, and an expression level of PAI-1; judging the risk of cancer recurrence based on the received activity value and expression level of the first CDK, the activity value and expression level of the second CDK, the expression level of uPA, and the expression level of PAI-1; and outputting the acquired judgment results.

According to the method of judging a risk of cancer recurrence of the present invention and the computer program, the risk of cancer recurrence in cancer patients can be judged more accurately. Therefore, it is expected that the present invention can provide an index for determining a course of treatment after treatment of the primary carcinoma to doctors.

BRIEF DESCRIPTION OF THE DRAWINGS

FIG. 1 is a block diagram showing a hardware configuration of a system for achieving the method of judging a risk of cancer recurrence of the present invention;

FIG. 2 is a flow chart showing a process of judging a risk of cancer recurrence by a computer;

FIG. 3 is a flow chart showing a process of judging a risk of cancer recurrence by a computer;

DETAILED DESCRIPTION OF THE PREFERRED EMBODIMENTS

Figure 4A:
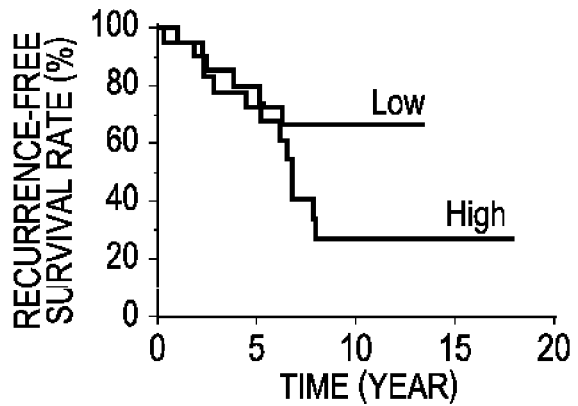
FIG. 4A shows graphs showing results obtained by classifying specimens extracted from breast cancer patients into a high risk group and a low risk group by conventional method 1 of judging a risk of cancer recurrence and analyzing the lifetime of each group.

The preferred embodiments of the present invention will be described hereinafter with reference to the drawings.

The term "recurrence" used herein means both the case where a primary carcinoma is treated and then the same cancer develops in the site of the primary focus and/or around thereof (local recurrence) and the case where cancer cells are separated from a primary focus and transferred to distant tissues (distant organs), and cancer develops therein (metastatic recurrence).

The term "risk of recurrence" used herein means both a risk of cancer recurring in the body of patients whose primary carcinoma have been treated and a risk of dying of patients due to cancer recurrence.

The term "recurrence risk score" used herein means an index to numerically evaluate the risk of cancer recurrence as a probability of recurrence.

The cycline-dependent-kinase (CDK) is a generic term for kinase activated by binding to cyclin and is known to be involved in the regulation of cell cycle progression.

The urokinase plasminogen activator (uPA) is a kind of serine protease and activates with plasminogen as a substrate. It is known that uPA binds to a urokinase receptor present on the cell surface and induces signal transmission which is involved in the growth and transfer of tumor.

The plasminogen activator inhibitor 1 (PAI-1) is a molecule which eliminates the activity of tissue plasminogen activator (tPA) in blood and inhibits the fibrinolytic system. Since PAI-1 rapidly binds to tPA released from endothelial cells and inhibits the activity, it is known as a factor which specifies the fibrinolytic activity in the blood.

The term "activity value of CDK" used herein means a kinase activity level (U) (unit is abbreviated as (U)) which is calculated from an amount of a substrate phosphorylated by the activated CDK.

The term "expression level" used herein means a value reflecting the amount of protein or mRNA contained in the biological sample (measurement sample). The expression level may be a measured value itself or a value calculated based on the measured value. The expression level may be represented by any form or unit (e.g., mass (weight), concentration, ratio, strength, and level).

[1] Method of Judging Risk of Cancer Recurrence (1-1) Biological Samples

In the method of judging a risk of cancer recurrence of the present invention (hereinafter also referred to as a "judgment method"), the activity value and expression level of the first CDK, the activity value and expression level of the second CDK, the expression level of uPA, and the expression level of PAI-1 are acquired from biological samples extracted from cancer patients.

In the embodiments of the present invention, the biological samples are not particularly limited as long as they are extracted from cancer patients and contain cells of the patients. It is preferable to use samples containing cancer cells such as tumor tissues. Examples of the biological samples include tissues of various internal organs, such as stomach, lung, heart, liver, kidney, pancreas, large intestine, uterus, and ovary; and mammary tissue, prostatic glandular tissue, thyroid tissue, lymph node tissue, muscle tissue, nervous tissue, cartilage tissue, osseous tissue, skin tissue, blood, bone marrow, body fluid, and coelome lavage fluid. Among them, the mammary tissue and the large intestine tissue are preferred, and the mammary tissue is more preferable.

In the embodiments of the present invention, the type of cancer in patients is not particularly limited. Examples thereof include gastric cancer, lung cancer, liver cancer, kidney cancer, pancreatic cancer, colon cancer, uterine cancer, ovarian cancer, breast cancer, prostatic cancer, thyroid cancer, lymphoma, oral cancer, skin cancer, brain tumor, leukemia, and myeloma. Among them, breast cancer and colon cancer are preferred, and breast cancer is more preferred.

(1-2) Acquisition of Activity Value of CDK

In the embodiments of the present invention, in order to acquire the activity value and expression level of the first CDK, the activity value and expression level of the second CDK, and the expression levels of uPA and PAI-1, it is desirable to prepare measurement samples from the biological samples. As described later, such measurement samples can be prepared by any known method in the art.

In the embodiments of the present invention, the activity values of the first and second CDKs can be acquired by measuring CDK kinase activity in the measurement samples prepared from the biological samples. The first and second CDKs are appropriately selected from CDKs known in the art. Preferably, they are selected from the group consisting of CDK1, CDK2, CDK4, CDK6, a cyclin A-dependent kinase, a cyclin B-dependent kinase, and a cyclin D-dependent kinase. In a more preferred embodiment, the first CDK is CDK1 and the second CDK is CDK2.

A sample for measuring CDK activity can be prepared, for example, by appropriately crushing a biological sample in a buffer solution. The method of crushing a sample is not particularly limited and it can be appropriately selected from any known method in the art. Examples thereof include an aspiration/discharge method using a pipette, a cell-crushing method by freezing and thawing, a stirring method using a vortex mixer, a crushing method using a blender, a compression method using a pestle, and an ultrasonic treatment using an ultrasonic treatment apparatus. Alternatively, the sample for measuring CDK activity may be prepared by mixing a biological sample with a solubilized liquid containing an appropriate surfactant and dissolving cells in the sample.

The buffer solution and the solubilized liquid are not particularly limited as long as they do not degrade and modify target protein extracted from cells in the biological sample. The buffer material to be used for the buffer solution and the surfactant contained in the solubilized liquid are known in the art and they can be appropriately selected according to the type of the biological samples. Examples of the buffer include phosphoric acid buffers, acetic acid buffers, citric acid buffers, MOPS (3-morpholinopropanesulfonic acid), HEPES(2-[4-(2-hydroxyethyl)-1-piperazinyl]ethane sulfonic acid), Tris(tris(hydroxymethyl)aminomethane), and Tricine (N-[tris(hydroxymethyl)methyl]glycine). Examples of the surfactant include Nonidet P-40 (NP-40) (registered trademark of Shell International Petroleum Company Limited), Triton-X (registered trademark of UnionCarbide Chemicals and Plastics Inc.), Tween (registered trademark of ICI Americas Inc.), Brij (registered trademark of ICI Americas Inc.), and Emulgen (registered trademark of Kao Corporation).

The solubilized liquid preferably contains the same buffer as the buffer solution. The buffer solution and the solubilized liquid may further contain protease inhibitors, phosphatase inhibitors, reductants known in the art, if necessary.

In the embodiments of the present invention, it is preferable to specifically recover a target CDK from the measurement sample prepared in the above manner. An anti-CDK antibody which specifically recognizes and binds to the target CDK may be used to recover the CDK. Alternatively, an anti-cyclin antibody which specifically recognizes and binds to cyclin binding to the target CDK may be used. In the cases of using both of the antibodies, CDKs other than active type CDK may be contained in the recovered CDK. For example, a complex having a CDK inhibitor bound to a complex of cyclin and CDK is also contained in the recovered CDK. When the anti-CDK antibody is used, a single CDK molecule (inactive type CDK), a complex of CDK and cyclin and/or CDK inhibitor, and a complex of CDK and another compound, and the like are contained in the recovered CDK. Therefore, in the embodiments of the present invention, the activity value of CDK is measured as a unit (U) of a substrate phosphorylated in a state where the active type CDK, the inactive CDK, and various competitive substances are mixed.

In the embodiments of the present invention, the method of acquiring the activity values of the first and second CDKs can be appropriately selected from measurement methods known in the art. For example, the activity value of CDK can be acquired by a method including mixing a measurement sample prepared from a biological sample, a CDK substrate, and a phosphate-group donor, detecting the substrate phosphorylated by the active type CDK, and quantifying the unit amount of the substrate. In the method, a phosphate group of the phosphate-group donor is incorporated into the substrate by the reaction through the active type CDK and thus the activity value of CDK can be acquire by quantifying the phosphorylated substrate.

More specific examples of the measurement method include the followings. First, a substrate protein is labeled by reacting a measurement sample, a substrate protein, and a phosphate-group donor ($\gamma$-[32P]-ATP) labeled with a radioisotope and incorporating 32P into the substrate protein. The radiation intensity of the 32P-labeled-phosphorylated substrate protein is measured. The unit amount of the phosphorylated substrate protein is quantified using the acquired measured value and a calibration curve prepared in advance from the measurement results of a CDK reference standard with a known concentration.

Examples of a non-radioisotope-based method include the methods disclosed in US2002/0164673 and 2007/0264624. In the methods, a measurement sample, a substrate protein, and adenosine 5'-O-(3-thiotriphosphate) (ATP-$\gamma$S) are reacted. The reaction results in introduction of a mono-thiophosphate group into a serine or threonine residue of the substrate protein. A labeling fluorescent substance or labeling enzyme is bound to a sulfur atom of the introduced mono-thiophosphate group. Thus, the substrate protein is labeled. The labeled amount of the thiophosphorylated-labeled substrate protein (the fluorescence intensity of the labeling fluorescent substance or the activity of the labeling enzyme) is measured. The unit amount of the phosphorylated substrate protein is quantified using the acquired measured value and a calibration curve prepared in advance from the measurement results of a CDK reference standard with a known concentration.

The substrate which is phosphorylated by the active type CDK is known in the art. The substrate for the active type CDK1 and the active type CDK2 includes histone H1. The substrate for the active type CDK4 and the active type CDK6 includes Rb (retinoblastoma protein).

(1-3) Acquisition of Expression Level

In the embodiments of the present invention, the expression levels of the first and second CDKs and the expression levels of uPA and PAI-1 can be acquired by measuring measurement samples prepared from biological samples by any known method in the art. The expression levels of the first and second CDKs and the expression levels of uPA and PAI-1 may be either the protein expression level or the mRNA expression level. The protein expression level is preferred.

In the embodiments of the present invention, the measurement samples prepared to acquire the activity value of CDK can be used as the measurement sample for acquiring the expression levels of proteins of the first and second CDKs and the expression levels of proteins of uPA and PAI-1.

The expression levels of proteins of the first and second CDKs and the expression levels of proteins of uPA and PAI-1 which are contained in the measurement samples can be measured by, for example, an enzyme-linked immunosorbent assay (ELISA) or a Western blot process or methods of quantifying proteins disclosed in US2004/0214180. In these methods, in order to trap the proteins of the first and second CDKs and the proteins of uPA and PAI-1, an antibody which specifically recognizes and binds to each of the proteins is used. For example, when an anti-CDK1 antibody is used, all forms of CDK1 (including a single CDK1 molecule, a complex of CDK1 and cyclin and/or CDK1 inhibitor, and a complex of CDK1 and another compound) contained in the measurement samples are trapped.

The expression levels of proteins of uPA and PAI-1 may be acquired using a commercially available measurement kit, e.g., FEMTELLE (registered trademark) (American Diagnostica Inc.).

In the embodiments of the present invention, when the mRNA expression levels of the first and second CDKs and the mRNA expression levels of uPA and PAI-1 are acquired, a measurement sample containing RNA can be prepared by any known method in the art. For example, the measurement sample containing RNA can be prepared by subjecting a biological sample to a physical process (stirring, homogenization, ultrasonic fragmentation) in an appropriate pretreatment liquid and releasing RNA contained in cells in the sample in solution.

As for the measurement samples thus obtained, tissues and residues of cells may be removed from the measurement sample, if necessary, by any known method in the art, such as centrifugation, filtering or column chromatography. Further, RNA contained in the measurement sample may be purified. For example, the measurement sample containing RNA isolated from cells is centrifuged to recover a supernatant. The supernatant is subjected to a phenol/chloroform extraction method to purify RNA. The preparation of measurement samples and the purification of RNA can be performed using a commercially available RNA extraction/purification kit.

In the embodiments of the present invention, the mRNA expression levels of the first and second CDKs and the mRNA expression levels of uPA and PAI-1 can be acquired by any known method in the art, such as a nucleic acid amplification method. These mRNA expression levels can be acquired by a microarray hybridization method. In the method, a microarray in which nucleic acid probes complementary to base sequences of the genes coding for proteins of the first and second CDK and proteins of uPA and PAI-1 are arranged is used. Among these methods, the nucleic acid amplification method is preferred to acquire the mRNA expression levels.

(1-4) Judgment of Risk of Cancer Recurrence

In the judgment method of the present invention, the risk of cancer recurrence is judged in the above manner based on the acquired activity value and expression level of the first CDK, the activity value and expression level of the second CDK, the expression level of uPA, and the expression level of PAI-1.

In an embodiment of the present invention, the recurrence risk score is acquired based on the activity value and expression level of the first CDK and the activity value and expression level of the second CDK in the judging step and the risk of cancer recurrence is judged based on the acquired recurrence risk score, the expression level of uPA, and the expression level of PAI-1.

The recurrence risk score can be acquired based on Equation (1) below.

$$(\text{Recurrence risk score}) = F(x) \times G(y) \quad (1)$$

(wherein x represents a first CDK specific activity, the first CDK specific activity is expressed by a first CDK activity value/first CDK expression level; y represents a specific activity ratio, the specific activity ratio is expressed by a second CDK specific activity/first CDK specific activity, and the second CDK specific activity is expressed by a second CDK activity value/second CDK expression level.)

The F(x) and G(y) are functions of x and y and represented by Equations (2) and (3) below.

$$F(x) = a/(1 + \text{Exp}(-(x1-b)xc)) \quad (2)$$

$$G(y) = d/(1 + \text{Exp}(-(y1-e)xf)) \quad (3)$$

(wherein, a, b, and c are constants defined by a correlation between x and a cancer recurrence rate; and d, e, and f are constants defined by a correlation between y and a cancer recurrence rate.)

Equation (2) is an equation obtained when changes in the recurrence rate to the CDK1 specific activity value are fitted by a logistic curve. A constant a (for example, 0.15) means the highest recurrence rate that can be given by the CDK1 specific activity value (for example, 15%). Constants b and c specify a shape of the curve.

Equation (3) is an equation obtained when changes in the recurrence rate to a ratio of the CDK2 specific activity value and the CDK1 specific activity value are fitted by a logistic curve. A constant d (for example, 0.25) means the highest recurrence rate that can be given by the specific activity ratio (for example, 25%). The constants e and f specify a shape of the curve.

In the embodiments of the present invention, the recurrence risk score is a value specified by two factors of the first CDK specific activity and the specific activity ratio, as represented by Equation (1) above. Here, the CDK specific activity and the specific activity ratio will be described.

The CDK specific activity is the ratio of the activity value to the expression level of CDK as being understood from the fact (CDK activity value)/(CDK expression level). That is, the CDK specific activity corresponds to the percentage of CDK exhibiting kinase activity among CDKs present in cells in biological samples. Therefore, the CDK specific activity reflects the CDK activity level based on the growth of cancer cells.

The specific activity ratio is the ratio of the second CDK specific activity to the first CDK specific activity as being understood from the fact that the ratio is expressed by a second CDK specific activity/first CDK specific activity. The period when CDK exhibits activity in the cell cycle varies depending on the type of CDK. Therefore, the specific activity ratio shows a ratio of activity levels of two types of CDKs which exhibit activities in a prejudged period of the cell cycle. Therefore, the specific activity ratio reflects which CDK activity in cancer patient's cells is predominant, namely, the percentage of cells present in each cell cycle.

Generally, a cancer cell is out of normally controlled growth and proliferates rapidly. Thus, when the ratio of cells staying in the period between S phase (DNA replicative period) and G2 phase (period of from termination of DNA synthesis to initiation of mitotic division) is high, the cells can be estimated to become cancerous. Aneuploidy and ploidy are considered to be caused by passing through an abnormal M phase (cell division stage), or proceeding to G1 phase and then S phase without undergoing M phase. In other words, the cells in which the ratio of cells in M phase is low may be estimated to become cancerous.

Therefore, for example, when CDK1 exhibiting activity when shifting from G2 phase to M phase is defined as a first CDK, CDK2 exhibiting activity when shifting from G1 phase to S phase is defined as a second CDK, and a CDK specific activity ratio is calculated based on the activity values and expression levels of the first and second CDKs, the acquired specific activity ratio is a value reflecting the proportion of cells in S phase or G2 phase to cells in M phase. Therefore, the specific activity ratio can be used as an index which accurately reflects the growth potential of cells.

The present inventors have found that the probability of cancer recurrence increases in proportion to the first CDK specific activity or a ratio of the first CDK specific activity to the second CDK specific activity. Then, the present inventors have acquired Equations (2) and (3) above as functions regarding the first CDK specific activity and the ratio of the first CDK specific activity to the second CDK specific activity by approximating the probability of recurrence using a logistic function (see Patent document 2).

As described above, the specific activity and specific activity ratio of CDK are an index reflecting the proliferative state and growth potential in cancer cells. In the embodiments of the present invention, the recurrence risk score is specified as a value which can be acquired from the product between Equation (2) regarding the first CDK specific activity and Equation (3) regarding the ratio of the first CDK to the second CDK specific activity.

In the embodiments of the present invention, the risk of cancer recurrence is judged by comparing each value thus acquired with a threshold set in advance. Specifically, when the recurrence risk score is less than the first threshold, the expression level of uPA is less than the second threshold, and the expression level of PAI-1 is less than the third threshold, the risk of cancer recurrence is judged to be low. When the recurrence risk score is higher than the first threshold, the expression level of uPA is higher than the second threshold, or the expression level of PAI-1 is higher than the third threshold, the risk of cancer recurrence is judged to be high.

In the preferred embodiment of the present invention, the first CDK specific activity is further used to judge the risk of cancer recurrence. That is, in the judgment step, the first CDK specific activity expressed by a first CDK activity value/first CDK expression level is acquired, and the risk of cancer recurrence is judged based on the acquired first CDK specific activity, the recurrence risk score, the expression level of uPA, and the expression level of PAI-1.

In this embodiment, when the recurrence risk score is less than the first threshold, the expression level of uPA is less than the second threshold, the expression level of PAI-1 is less than the third threshold, and the first CDK specific activity is less than the fourth threshold, the risk of cancer recurrence is judged to be low. When the recurrence risk score is higher than the first threshold, the expression level of uPA is higher than the second threshold, the expression level of PAI-1 is higher than the third threshold, or the first CDK specific activity is higher than the fourth threshold, the risk of cancer recurrence is judged to be high.

The first, second, third, and fourth thresholds can be appropriately set according to the kind of cancer in patients being judged. That is, the thresholds can be experientially set as prejudged values which can distinguish a patient group with cancer recurrence and a patient group without cancer recurrence. For example, as for biological samples which are extracted from patients with cancer recurrence and patients without cancer recurrence after a fixed time from biological sample extraction, the activity value and expression level of the first CDK, the activity value and expression level of the second CDK, the expression level of uPA, and the expression level of PAI-1 are acquired. The recurrence risk score, the expression levels of uPA and PAI-1, and the first CDK specific activity are acquired from these values. Respective values of the recurrence risk score which can distinguish between patients whose cancer has recurred and patients whose cancer has not recurred, the expression level of uPA, the expression level of PAI-1, and the specific activity of first CDK can be set to a first threshold, a second threshold, a third threshold, and a fourth threshold, respectively.

In the embodiments of the present invention, values known in the art may be used as the thresholds. For example, in the method of judging a risk of recurrence of breast cancer, when the first and second CDKs are CDK1 and CDK2, respectively, the threshold of the recurrence risk score is 0.45, and the threshold of the first CDK specific activity is 70 (maU/eU). Further, in the method of judging a risk of recurrence of breast cancer, the thresholds of the expression levels of uPA and PAI-1 are 3 (ng/mg whole protein) and 14 (ng/mg whole protein), respectively in the case of measurement by the ELISA method. The thresholds of the expression levels of uPA and PAI-1 for breast cancer are established as international standards.

[2] Computer Program for Judging Risk of Cancer Recurrence

Hereinafter, the computer program to allow a computer to execute the method of judging a risk of cancer recurrence (hereinafter simply referred to as a "program") will be described.

As one embodiment of the present invention, a hardware configuration of a system to judge the risk of cancer recurrence which includes a judgment device 100 for executing the program and a measurement device 200 for measurement samples is shown in FIG. 1.

The system to judge the risk of cancer recurrence includes the judgment device 100 and the measurement device 200 for measurement samples and these devices are connected by a cable 300. The judgment device 100 receives the activity value and expression level of the first CDK, the activity value and expression level of the second CDK, the expression level of uPA, and data of the expression level of PAI-1 which are measured by the measurement device 200 (hereinafter also referred to as "data of cancer patients") via the cable 300. The judgment device 100 analyzes the data output from the measurement device 200, judges the sensitivity to a patient's risk of cancer recurrence, and outputs the judgment results.

The measurement device 200 may be configured to include a plurality of measurement devices. For example, the measurement device 200 is configured by a device which measures the kinase activity of CDK, a device which measures the expression level of CDK, and a device which measures the expression levels of uPA and PAI-1. The judgment device 100 and the measurement device 200 may be configured as an integrated device.

The configuration of the judgment device 100 will be described. The judgment device 100 is mainly configured by a main body 110, a display unit 120, and an input device 130. In the main body 110, a Central Processing Unit (CPU) 110a, a Read Only Memory (ROM) 110b, a Random Access Memory (RAM) 110c, a hard disk 110d, a read-out device 110e, an input/output interface 110f, an image output interface 110g are data-communicably connected to one another by a bus 110h.

The CPU 110a can execute computer programs stored in the ROM 110b and the computer programs loaded in the RAM 110c. The ROM 110b is configured by mask ROM, PROM, EPROM, EEPROM, and the like. Further, on the ROM 110b, computer programs to be executed by the CPU 110a, data used for the execution of the computer programs are recorded.

The RAM 110c is configured by Static Random Access Memory (SRAM) or Dynamic Random Access Memory (DRAM), and the like. The RAM 110c is used to read out the computer programs recorded on the ROM 110b and the hard disc 110d. In executing these computer programs, the RAM 110c is used as a work region of the CPU 110a.

The hard disc 110d is installed with various computer programs to be executed by the CPU 110a such as operating system and application system program, as well as data used in executing the computer program. A computer program 140a to allow the judgment device 100 to execute the judgment method of the present invention and each threshold data to be used for judgment are installed in the hard disk 110d.

The read-out device 110e is configured by flexible disc drive, Compact Disc (CD)-ROM drive, Digital Versatile Disc (DVD)-ROM drive, and the like. The read-out device 110e is able to read out computer programs or data recorded on the portable recording medium 140.

The application program 140a which executes the operation by the computer and each threshold data are stored in the portable recording medium 140. The CPU 110a can read out the application program 140a from the portable recording medium 140 and install the application program 140a and each threshold data to the hard disk 110d.

Operating system providing graphical interface environment such as Windows (registered trademark) manufactured and sold by US Microsoft Co. is installed in the hard disc 110d.

Hereinafter, the program (computer program 140a) of the present invention which is assumed to be operating on the operating system will be described.

The input/output interface 110f includes a serial interface such as Universal Serial Bus (USB), IEEE1394, and RS-232C; a parallel interface such as SCSI, IDE, and IEEE1284; and an analog interface such as D/A converter and A/D converter. The input/output interface 110f is connected to the input device 130 including a keyboard and a mouse. Users can use the input device 130 to input data of cancer patients acquired by measurement of a test sample into the main body 110 of the computer. A measurement device 200 is connected to the input/output interface 110f. The data of cancer patients acquired by measurement of a test sample by the measurement device 200 is directly sent from the measurement device 200 to the main body 110 of the computer.

The image output interface 110g is connected to the display unit 120 configured by LCD, CRT or the like, and outputs an image signal corresponding to the image data input from the CPU 110a. The display unit 120 outputs image data based on the input image signal. The display unit 120 outputs judgment results input from the CPU 110a.

Hereinafter, as one embodiment of the present invention, a processing flow of the computer program 140a which is executed in the judgment device 100 will be described with reference to FIG. 2.

The measurement device 200 directly sends the data of cancer patients acquired by measurement of a test sample to the main body 110 of the computer.

The CPU 110a of the judgment device 100 receives data of the activity value and expression level of the first CDK, the activity value and expression level of the second CDK, the expression level of uPA, and the expression level of PAI-1 from the measurement device 200 via the input/output interface 110f (step S1). The CPU 110a stores the acquired data in the RAM 110c.

The CPU 110a reads out the data stored in the RAM 110c and calculates the recurrence risk score (step S2). The CPU 110a stores the calculated recurrence risk score in the RAM 110c. In the step S2, it is preferably that the CPU 110a further calculates the first CDK specific activity.

The CPU 110a reads out the first, second, and third thresholds which have been stored in the hard disk 110d in advance. Then, the CPU 110a compares the first threshold with the recurrence risk score (step 3-1). When the recurrence risk score is lower than the first threshold (Yes), the process is advanced to the step S3-2. On the other hand, when the recurrence risk score is not lower than the first threshold (No), the process is advanced to the step S4-2.

In the step 3-2, the CPU 110a compares the second threshold with the expression level of uPA. When the expression level of uPA is lower than the second threshold (Yes), the process is advanced to the step S3-3. On the other hand, when the expression level of uPA is not lower than the second threshold (No), the process is advanced to the step S4-2.

In the step 3-3, the CPU 110a compares the third threshold with the expression level of PAI-1. When the expression level of PAI-1 is lower than the third threshold (Yes), the process is advanced to the step S4-1. On the other hand, when the expression level of PAI-1 is not lower than the third threshold (No), the process is advanced to the step S4-2.

When the first CDK specific activity is calculated in the step 2, it is preferable that the CPU 110a reads out the fourth threshold which has been stored in the hard disk 110d in advance and compares the fourth threshold with the first CDK specific activity (step 3-4 of FIG. 3). When the first CDK specific activity is lower than the fourth threshold (Yes), the process is advanced to the step S4-1. On the other hand, when the first CDK specific activity is not lower than the first threshold (No), the process is advanced to the step S4-2.

As being understood from FIGS. 2 and 3, the order of the steps 3-1, 3-2, 3-3, and 3-4 can be changed in the process flow. In the description, the data of cancer patients has been sent from the measurement device 200 to the main body 110 of the computer, however the present invention is not limited to the embodiment. For example, the data of cancer patients may be input to the main body 110 of the computer via the input/output interface 110f by user's input operation to the input device 130.

Each of the thresholds can be set according to the type of cancer in patients. The thresholds set in this embodiment are shown in Table 1 below, however they are not limited thereto.

TABLE 1

| Term | Threshold |
| --- | --- |
| Recurrence risk score | 0.45 |
| Expression level of μPA | 3 (ng/mg) |
| Expression level of PAI-1 | 14 (ng/mg) |
| First CDK specific activity | 70 (maU/eU) |

In this embodiment, each threshold has been stored in the hard disk 110d in advance, however the present invention is not limited to the embodiment. For example, the CPU 110a can receive the data of each threshold input from the input device via the input/output interface 110f. The CPU 110a can also receive the data of each threshold stored in an external storage device via the input/output interface 110f connected to the Internet. Further, the read-out device reads out the data of each threshold recorded in the portable recording medium 140 so that the CPU 110a can receive the data.

When the recurrence risk score is less than the first threshold, the expression level of uPA is less than the second threshold, and the expression level of PAI-1 is less than the third threshold, the CPU 110a judges that the risk of cancer recurrence is low (step S4-1). When the recurrence risk score is higher than the first threshold, the expression level of uPA is higher than the second threshold, or then expression level of PAI-1 is higher than the third threshold, the CPU 110a judges that the risk of cancer recurrence is high (step S4-2).

In the case where the first CDK specific activity is calculated in the step 2, when the recurrence risk score is less than the first threshold, the expression level of uPA is less than the second threshold, the expression level of PAI-1 is less than the third threshold, and the first CDK specific activity is less than the fourth threshold, the CPU 110a judges that the risk of cancer recurrence is low (step S4-1). Further, when the recurrence risk score is higher than the first threshold, the expression level of uPA is higher than the second threshold, the expression level of PAI-1 is higher than the third threshold or the first CDK specific activity is higher than the fourth threshold, the CPU 110a judges that the risk of cancer recurrence is high (step S4-2).

The CPU 110a stores the judgment results in the hard disk 110d and outputs the display unit 120 via the image output interface 110g (step S5).

Here, the CPU 110a has output only the judgment results. The CPU 110a may output instructions as to whether an adjuvant therapy is performed on cancer patients whose biological samples have been extracted. That is, when the CPU 110a has judged that the risk of cancer recurrence is low, it outputs the judgment results and instructions which do not perform the adjuvant therapy to the display unit 120.

EXAMPLE

Example 1

Example 1 aims at examining the risk of cancer recurrence in biological samples in which the presence of cancer recurrence after extraction of the biological samples is confirmed by the judgment method of the present invention and conventional judgment methods and examining the judgment accuracy.

In this example, as the conventional judgment methods, a method based on the activity value and the expression level of the first and second CDKs (hereinafter referred to as a "conventional method 1") and a method based on the expression levels of uPA and PAI-1 (hereinafter referred to as a "conventional method 2") were used.

(1) Biological Samples

As biological samples, tissues (39 specimens) extracted from 39 breast cancer patients were obtained from a tumor bank managed by the medical department of the Technical University Munich. Various clinical information on the 39 specimens, such as therapeutic methods performed on patients and the presence of cancer recurrence after specimen extraction was acquired. These 39 specimens were selected so that a ratio of cases in which cancer recurred after specimen extraction and cases in which recurrence was not observed for a constant period was approximately 1:1. That is, in this example, the cancer recurrence rate is set to about 50%.

(2) Preparation of Measurement Samples

Specimens (50 to 3000 mg) and crushing balls were put into tubes. The specimens were ground at a rotational speed of 3000/min for 30 seconds with a crusher (Mikro-Dismembrator S; manufactured by Sartorius AG). 1 mL of a solubilized liquid (tris buffered saline (TBS), pH 8.5) was added to the tubes. The tubes were rotated at 4° C. for 4 hours to solbilize the specimens. Each tube was centrifuged (100,000×g, 4° C., 4 hours), and the obtained supernatants were recovered as measurement samples. The obtained measurement samples were cryopreserved until they were used for each measurement.

(3) Acquisition of Expression Levels of First and Second CDKs (3-1) Solid-Phase Formation of Protein on Filter Plate 100 μL of 30% ethanol was added to each well of a filter plate to measure the expression level (Filter Plate Multi-Screen HTS PSQPlate; manufactured by Millipore). The plate was placed in an aspirator (a pump for aspiration/pressurization and a multiscreen HTS vacuum manifold; manufactured by Millipore), the setting of the aspirator was "−5-in Hg", and the solution in each well was aspirated (hereinafter, the setting of the aspirator was "−5-in Hg" and the aspiration was performed). A valve of the apparatus was closed after aspiration and the plate was detached from the manifold. 200 μL of a membrane wash solution (25 mM Tris-HCl (pH 7.4), 150 mM NaCl) was added to each well of the plate. The plate was placed in the manifold and the solution in each well was aspirated. 100 μL of a diluent of the measurement sample was dispensed in each well. 100 μL of a reference standard solution of CDK to prepare a calibration curve was dispensed in each well.

The diluent of the measurement sample was prepared as follows. As the reference standard solution of CDK, CDK1 and CDK2 solutions having the following concentrations were used.

Diluent of measurement sample (800 μL)

| Membrane wash solution (25 mM Tris-HCl (pH 7.4), 150 mM NaCl) | 475 μL |
| Specimen diluted solution (0.005% NP-40, 25 mM Tris-HCl (pH 7.4), 150 mM NaCl) | 300 μL |
| Measurement samples | 25 μL |
| Total | 800 μL |

Reference standards of CDK1: 340 and 170, and 85 ng/mL of three-point dilution series Reference standards of CDK2: 130 and 65, and 32.5 ng/mL of three-point dilution series The reference standard solutions of CDK having each concentration were dispensed in 2 wells. The diluent of the measurement sample was dispensed in 3 wells for each specimen. As a control, 100 μL of the specimen diluent was dispensed in 4 wells.

After dispensing, the plate was placed in the manifold. The proteins in the solution were adsorbed to the filter plate by aspirating the solution in each well. 300 μL of the membrane wash solution was added to each well, and then the solution was again aspirated to clean the filter plate.

(3-2) Antigen-Antibody Reaction and Fluorescent Labeling Reaction on Filter Plate 100 μL of a blocking reagent (4% BSA, TBS (pH 7.4)) was dispensed in each well of the filter plate and the solution was aspirated. 300 μL of the membrane wash solution was added to each well, and then the solution was again aspirated to clean the filter plate.

50 μL of anti-CDK1 polyclonal antibody (120 μg/mL) was dispensed in each well to measure the expression level of CDK1. 50 μL of anti-CDK2 polyclonal antibody (75 μg/mL) was dispensed in each well to measure the expression level of CDK2. Then, the solution in each well was aspirated. 50 μL of each of the antibody solutions was again added and incubated in an incubator set at 23° C. for 2 hours. The plate was placed in the manifold and the solution in each well was aspirated. The cleaning process including adding 300 μL of the membrane wash solution to each well and aspirating the solution was repeated 4 times.

50 μL of a secondary antibody reagent (biotinylated anti-rabbit IgG antibody (8 μg/mL); trade name: Goat Anti-Rabbit IgG(H+L)-BIOT Human/Mouse Adsorbed, manufactured by Southern Biotech, model number: 4050-08) was dispensed in each well and the solution was aspirated. 50 μL of the secondary antibody reagent was again added and incubated in an incubator set at 23° C. for 45 minutes. The plate was placed in the manifold and the solution in each well was aspirated. The cleaning process including adding 300 μL of the membrane wash solution to each well and aspirating the solution was repeated 2 times. 100 μL of a fluorescent labeling reagent (FITC labeled streptavidin (10 μg/mL); trade name: FLUO-RESEIN STREPTAVIDIN, manufactured by VECTOR, model number: SA5001) was added to each well of the plate and the solution in each well was aspirated. The cleaning process including adding 300 μL of the membrane wash solution to each well and aspirating the solution was repeated 4 times. After cleaning, an underdrain of the filter plate was detached. The bottom of the plate was pressed against the KIMTOWEL (registered trademark, NIPPON PAPER CRECIA Co., LTD.) to absorb the remaining solution. The plate was placed upside down in the incubator set at 60° C. and it was well dried.

(3-3) Fluorescence Detection

A plate leader (Infinite F200; manufactured by Tecan) was used to detect the fluorescence from fluorescently-labeled substances. The excitation wavelength and the fluorescence wavelength of the plate leader were set to 485 nm and 535 nm, respectively, and the fluorescence intensity of each well of the plate was measured. A calibration curve showing a relationship between the fluorescence intensity and the amount of CDK was prepared from the measured value of each well in which a reference standard solution of CDK was dispensed. The expression levels of CDK1 and CDK2 contained in the measurement samples were quantified from the calibration curve and the acquired measured value.

(4) Acquisition of Activity Values of First and Second CDKs (4-1) Preparation of 20% Protein A Bead Suspension Protein A beads (catalog No. 17-5280-04; GE health care) in a reagent container was subjected to end-over-end mixing to suspend the beads. An immunoprecipitation buffer (50 mM Tris-HCl (pH 7.4), 0.1% NP-40) was added thereto to prepare a 20% bead suspension.

(4-2) Capture of CDK Molecules by Immunoprecipitation

30 μL of the 20% protein A bead suspension was dispensed in each well of a filter plate for immunoprecipitation (product name: MultiScreen (registered trademark) HTS FilterPlate Hydrophilic, manufactured by Millipore, model number: MSHVN4550). An anti-CDK1 antibody (8 μg/well) was added to each well to acquire the activity value of CDK1 in the plate. An anti-CDK2 antibody (3 μg/well) was added to each well to acquire the activity value of CDK2. Rabbit IgG (5 μg/well) (CALBIOCHEM) was added to each well to measure the background. 90 μL of the diluent of the measurement sample prepared in the step (3-1) was dispensed in each well. 30 μL of the CDK reference standard solution to prepare a calibration curve was dispensed in each well. As the CDK reference standard solution, a three-point dilution series which was a mixed liquid of the CDK1 reference standard solutions (5, 2.5, and 1.25 ng) and the CDK2 reference standard solution (40, 20, and 10 ng) was used.

The filter plate was covered and immunoprecipitation was performed by stirring the plate for 120 minutes using a plate shaker in a low-temperature incubator at 4° C. After termination of the reaction, the filter plate was placed in the aspirator, the setting of the aspirator was "−5-in Hg", and the solution in each well was aspirated (hereinafter, the setting of the aspirator was "−5-in Hg" and the aspiration was performed). After aspiration, 200 µL of an immunoprecipitation wash solution 1 (50 mM Tris-HCl (pH 7.4), 1% NP-40) was dispensed in each well of the plate and the solution in each well was aspirated by the aspirator. 200 µL of the immunoprecipitation wash solution was again dispensed in each well and the solution in each well was aspirated by the aspirator. After aspiration, 200 µL of an immunoprecipitation wash solution 2 (50 mM Tris-HCl (pH 7.4), 300 mM NaCl) was dispensed in each well of the plate and the solution in each well was aspirated by the aspirator. 200 µL of an immunoprecipitation wash solution 3 (50 mM Tris-HCl (pH 7.4)) was dispensed in each well of the plate and the solution in each well was aspirated by the aspirator. The plate was pressed against the KIMTOWEL (registered trademark, NIPPON PAPER CRECIA Co., LTD.) to absorb the remaining solution.

(4-3) Enzyme Reaction

50 µL of an enzyme reaction reagent (200 µg/mL histone H1 protein, 5 mM ATP-γ-S and 20 mM Tris-HCl (pH 7.4)) was dispensed in each well of the plate after the cleaning operation. The plate was covered and enzyme reaction was performed by stirring at 900 rpm for 60 minutes using a constant temperature shaker at 37° C. This reaction leaded to the thiophosphorylation of histone H1 as a substrate protein. The plate was detached from the constant temperature shaker. A recovery plate (Rigid Plate V Bottom Non-Sterile Clear; manufactured by Sterilin) was stacked on a lower portion of the plate. The two stacked plates were centrifuged (at 4° C. and 2000 rpm for 5 minutes) to obtain a reaction product solution on the recovery plate.

(4-4) Fluorescent Labeling Reaction

14 µL of the reaction product solution recovered in the above manner was dispensed each well of a plate for fluorescent-labeling reaction (MicroAmpOptical 96-Well Reaction Plate; manufactured by Applied Biosystems). 14 µL of a fluorescent labeling reagent (400 nM 5-indoacetamide fluorescein) was dispensed in each well and the plate was stirred. Then, the plate was shaded by wrapping with aluminum foil. Fluorescent-labeling reaction was performed by stirring at 400 rpm for 20 minutes using the constant temperature shaker at 25° C. 200 µL of a reaction termination solution (2M MOPS, 60 mM N-acetylcysteine, pH 7.4) was dispensed in each well and stirred to terminate the fluorescent-labeling reaction.

(4-5) Solid-Phase Formation on Measuring Filter Plate

An underdrain at the back side of a filter plate to measure the activity (MultiScreen HTS FilterPlate, Hydrophobic; manufactured by Millipore) was slowly detached and placed in the aspirator. 100 µL of 70% ethanol was added to each well of the filter plate to measure the activity and the solution in each well was aspirated by the aspirator. The valve of the apparatus was closed after aspiration, and the pump was turned off. 200 µL of a membrane wash solution (25 mM Tris-HCl (pH 7.4), 150 mM NaCl) was added to each well of the plate and the solution in each well was aspirated by the aspirator. Then, the solution after the termination of the reaction in the plate for fluorescent-labeling reaction was transferred to each well of the plate to measure the activity. The valve of the aspirator was opened to aspirate the solution in each well of the plate to measure the activity. 300 µL of the membrane wash solution was dispensed in each well and the solution in each well was aspirated by the aspirator. The bottom of the plate was pressed against the KIMTOWEL (registered trademark, NIPPON PAPER CRECIA Co., LTD.) to absorb the remaining solution. The plate was placed upside down in the incubator set at 60° C. and it was well dried.

(4-6) Fluorescence Detection

A plate leader (Infinite F200; manufactured by Tecan) was used to detect the fluorescence from fluorescently-labeled substances. The excitation wavelength and the fluorescence wavelength of the plate leader were set to 485 nm and 535 nm, respectively, and the fluorescence intensity of each well of the plate to measure the activity was measured. A calibration curve showing a relationship between the fluorescence intensity and the activity of CDK was prepared from the measured value of each well in which a reference standard solution of CDK was dispensed. The activity values of CDK1 and CDK2 contained in the measurement samples were quantified from the calibration curve and the acquired measured value.

(5) Acquisition of Expression Levels of uPA and PAI-1

The expression levels of uPA and PAI-1 were acquired by measuring the diluent of the measurement sample prepared in the step (3-1) using ELISA measurement kits, manufactured by American Diagnostica (uPA ELISA kit (product number 894) and PAI-1-ELISA kit (product number 821)). The measurement was performed according to the manuals attached to the kits. Specifically, the details are as follows.

100 µL of the diluent of the measurement sample and 100 µL of a reference standard solution of uPA attached to the kit were added to each well of a microplate pre-coated with anti-uPA antibody. Similarly, 100 µL of the diluent of the measurement sample and 100 µL of a reference standard solution of PAI-1 attached to the kit were added to a plate pre-coated with anti-PAI-1 antibody. These plates were incubated at 4° C. overnight. Each well of each plate was cleaned with a buffer attached to the kit 4 times. 100 µL of anti-uPA antibody for detection was added to each well of a microplate pre-coated with anti-uPA antibody. Similarly, 100 µL of anti-PAI-1 antibody for detection was added to each plate pre-coated with anti-PAI-1 antibody. These plates were incubated at room temperature for 1 hour, and each well of each plate was cleaned with a cleaning buffer 4 times. 100 µL of enzyme conjugate diluent attached to the kit was added to each well. These plates were incubated at room temperature for 1 hour, and each well of each plate was cleaned with a cleaning buffer 4 times. 100 µL of a substrate solution attached to the kit was added to each well and incubated at room temperature for 20 minutes. 50 µL of 0.5N H2SO4 was added to each well to stop the reaction. The absorbance at 450 nm of each well was measured with the plate leader. A calibration curve showing a relationship between then absorbance and the expression level was prepared from the measured value of each well in which the reference standard solutions of uPA and PAI-1 were dispensed. The expression levels of uPA and PAI-1 contained in the measurement samples were quantified from the calibration curve and the acquired measured value.

(6) Judgment of Risk of Cancer Recurrence (6-1) Calculation of Recurrence Risk Score and Specific Activity of CDK1

The recurrence risk score (RRS) was calculated based on Equations (1) to (3) below using the expression levels and activity values of CDK1 and CDK2 thus obtained. The specific activity of CDK1 was calculated based on Equation (4) below.

$$(RRS) = 3000 \times F(x) \times G(y) \quad (1)$$

$$F(x) = 0.15/(1 + \text{Exp}(-(x-1.6) \times 7)) \quad (2)$$

$$G(y) = 0.25/(1 + \text{Exp}(-(y-1.0) \times 6)) \quad (3)$$

[wherein, in Equations (2) and (3), x=(CDK1 activity value)/(CDK1 expression level), and y=[(CDK2 activity value)×(CDK1 expression level)]/[(CDK2 expression level)×(CDK1 activity value]

$$\text{(CDK1 specific activity)} = \text{(CDK1 activity value)} / \text{(CDK1 expression level)} \quad (4)$$

Judgment of Risk of Recurrence by Conventional Method 1

In the judgment of the risk of recurrence by the conventional method 1, the calculated specific activities of RRS and CDK1 in each specimen were compared with their thresholds. Then, the cancer patients were classified into a high recurrence risk group (High group) and a low recurrence risk group (Low group). That is, the patients of the specimens in which the RRS was equal to or more than 0.45 or the CDK1 specific activity was equal to or more than 70 (maU/eU) were judged as the High group. The patients of the specimens in which the RRS was less than 0.45 and the CDK1 specific activity was less than 70 (maU/eU) were judged as the Low group.

Judgment of Risk of Recurrence by Conventional Method 2

In the judgment of the risk of recurrence by the conventional method 2, the acquired expression levels of uPA and PAI-1 in each specimen were compared with their thresholds. Then, the cancer patients were classified into a high recurrence risk group (High group) and a low recurrence risk group (Low group). That is, the patients of the specimens in which the expression level of uPA was equal to or more than 3 (ng/mg whole protein) or the expression level of PAI-1 was equal to or more than 14 (ng/mg whole protein) were judged as the High group. The expression level of uPA was less than 3 (ng/mg whole protein) and the expression level of PAI-1 was less than 14 (ng/mg whole protein) were judged as the Low group.

Judgment of Risk of Recurrence by Judgment Method of Present Invention

In the judgment of the risk of recurrence by the judgment method of the present invention, the calculated specific activities of RRS and CDK1 in each specimen and the acquired expression levels of uPA and PAI-1 were compared with their thresholds. Then, the cancer patients were classified into a high recurrence risk group (High group) and a low recurrence risk group (Low group). That is, the patients of the specimens in which the RRS was equal to or more than 0.45, the CDK1 specific activity was equal to or more than 70 (maU/eU), the expression level of uPA was equal to or more than 3 (ng/mg whole protein) or the expression level of PAI-1 was equal to or more than 14 (ng/mg whole protein) were judged as the High group. The patients of the specimens in which the RRS was higher than 0.45, the CDK1 specific activity was higher than 70 (maU/eU), the expression level of uPA was higher than 3 (ng/mg whole protein), and the expression level of PAI-1 was higher than 14 (ng/mg whole protein) were judged as the Low group.

Figure 4B:
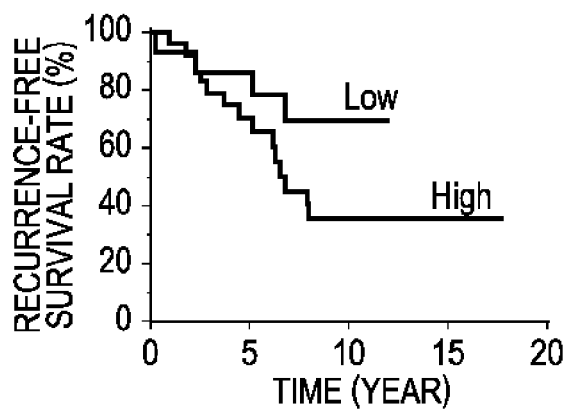
FIG. 4B shows graphs showing results obtained by classifying specimens extracted from breast cancer patients into a high risk group and a low risk group by conventional method 2 of judging a risk of cancer recurrence and analyzing the lifetime of each group.
Figure 4C:
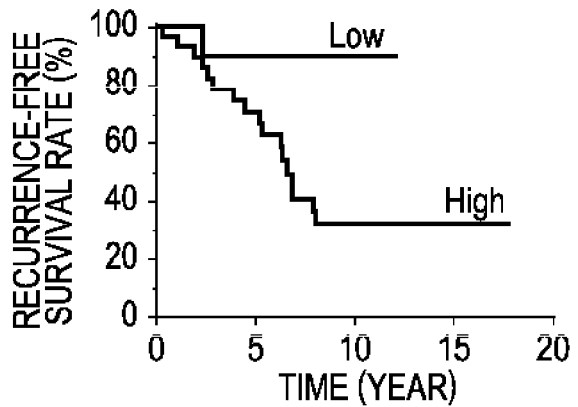
FIG. 4C shows graphs showing results obtained by classifying specimens extracted from breast cancer patients into a high risk group and a low risk group by the judgment method of the present invention and analyzing the lifetime of each group.

Lifetime analysis based on a log rank test was performed on each of the High and Low groups classified by the judgment method of the present invention, the conventional method 1, and the conventional method 2. The obtained results are shown in FIG. 4A-C. FIG. 4A shows the results by the conventional method 1, FIG. 4B shows the results by the conventional method 2, and FIG. 4C shows the results by the judgment method of the present invention.

In the conventional method 1, 12 cases (60%) of 20 cases classified into the High group and 6 cases (32%) of 19 cases classified into the Low group were specimens of patients died due to cancer recurrence. In the case of the conventional method 2, 14 cases (56%) of 25 cases classified into the High group and 4 cases (29%) of 14 cases classified into the Low group were specimens of patients died due to cancer recurrence. That is, in the case of the conventional methods 1 and 2, the recurrence-free survival rate after 5 years in the Low groups which were judged to have a low risk of recurrence was less than 90%. There was no statistically significant difference between the High groups and the Low groups which were classified by the conventional methods 1 and 2 (P=0.0976 and P=0.1, respectively).

On the other hand, in the method of the present invention, 17 cases (59%) of 29 cases classified into the High group and 1 case (10%) of 10 cases classified into the Low group were specimens of patients died due to cancer recurrence. That is, in the case of the judgment method of the present invention, the recurrence-free survival rate after 5 years in the Low group was 90%. There was a statistically significant difference between the High and Low groups (P=0.0087).

Therefore, the judgment method of the present invention has a judgment accuracy higher than those of the conventional methods. It was suggested that the combination of judgment items used in the judgment method could be a powerful predictive factor of the risk of recurrence.

As for the judgment method of the present invention, the conventional method 1, and the conventional method 2, the percentage of risk (hazard ratio: HR) was examined. The risk percentage of the Low group to the High group was calculated with Cox proportional hazard models. The results are shown in Table 2 below.

As is clear from Table 2, the risk percentages in the conventional methods 1 and 2 were 2.2 and 1.7, respectively. The risk percentage in the judgment method of the present invention was significantly high (9.2). It was suggested that since the value was higher than the sum (3.9) of the risk percentages of the conventional methods 1 and 2, the prediction performance of the risk of recurrence was synergistically improved in the judgment method of the present invention.

TABLE 2

| Judgment method | Hazard ratio | 95 percent confidence interval of hazard ratio | P value |
| --- | --- | --- | --- |
| Conventional method 1 | 2.2424 | 0.8391-5.9927 | 0.1092 |
| Conventional method 2 | 1.7150 | 0.6998-4.2030 | 0.2406 |
| Present invention | 9.2138 | 1.2316-68.9323 | 0.03141 |

REFERENCE EXAMPLE

The reference example aims at examining how much the judgment accuracy of the risk of cancer recurrence was improved when, as for the biological sample, various pathological diagnostic items were combined with the conventional method 1 or the conventional method 2.

The used pathological diagnostic items include patient's age, tumor diameter, presence of lymph node metastasis, histological grade classification, hormone receptor (progesterone receptor (PR)) expression, and Her2 expression. Thresholds for the risk classification of each item are shown in Table 3 below.

TABLE 3

| Term | Low group | High group |
|---|---|---|
| Age | 51 years old or older | 50 years old or younger |
| Tumor diameter | 2 cm or less | 2 cm or more |
| Lymph node metastasis | None | present |
| Histological grade classification | 1 or 2 | 3 |
| PR expression | Positive | Negative |
| Her2 expression | Negative | Positive |

In this reference example, the presence of lymph node metastasis and histological grade classification were judged by staining tissue sections of specimens by a general hematoxylin/eosin staining method and observing them with a microscope. The histological grade classification was performed in accordance with the judgment standard described in "Breast Cancer Vol. 16 Supplement" (edited by the Japanese Breast Cancer Society).

The expression of Her2 was judged by a general immunohistochemical staining method. The specific procedures are as follows. Specimen tissue sections were put on a slide glass pre-coated with aminosilane and dried at 37° C. overnight. The specimens were rehydrated with PBS and cleaned twice. The specimens were pretreated at room temperature for 30 minutes with 0.005% saponin (Sigma). The specimens were cleaned with PBS and reacted with anti-Her2 mouse monoclonal antibody (0.125 μg/mL; Oncogene Science) at 4° C. overnight. The specimens were cleaned with PBS and reacted with rabbit anti-mouse IgG (20 μg/mL; Dianova GmbH). The specimens were cleaned with PBS and reacted with alkaline phosphatase anti-alkaline phosphatase complex (50-fold dilution; Dianova) at room temperature for 30 minutes. The specimens were cleaned with PBS and reacted with Texas Fast Red (Sigma) which was a substrate of alkaline phosphatase. Further, the resultant product was counterstained with hematoxylin. The stained tissue sections were observed with a light microscope (4-fold objective lens). In this observation, the case where no Her2 positive cells was contained in the tissue sections or the number of the positive cells in all of the tumor cells in the tissue sections was less than 10% was judged to be negative. The case where the cell number was 10% or more was judged to be positive.

The expression of PR was judged by the immunohistochemical staining method using an antibody to PR, similarly to the case of Her2. Specific judgment procedures are as follows. The tissue sections of the stained specimens were observed with a light microscope (4-fold objective lens) to confirm nuclear PR immunoreactivity in tumor cells. When the number of cells with immunoreactivity in all of the tumor cells in the tissue sections was less than 10% was judged to be negative. The case where the cell number was 10% or more was judged to be positive.

The above items and the hazard ratios when judging the risk of cancer recurrence by the conventional methods 1 and 2 (Low group versus High group, Cox proportional hazard model) are shown in Table 4 below.

TABLE 4

| Term | HR |
|---|---|
| Age | 1.303 |
| Tumor diameter | 1.545 |
| Lymph node metastasis | 4.854 |
| Histological grade classification | 1.219 |
| PR expression | 1.416 |
| Her2 expression | 0.896 |
| Conventional method 1 | 2.242 |
| Conventional method 2 | 1.720 |

When various pathological diagnostic items are combined with the conventional method 1, the risk of cancer recurrence in patients was judged in the following manner. The patients of specimens judged to be a low risk by both of the conventional method 1 and the pathological diagnostic items were judged as the Low group. The patients of specimens judged to be a high risk by either the conventional method 1 or the pathological diagnostic items were judged as the High group.

When the conventional method 2 was combined with various pathological diagnostic items, the risk of cancer recurrence in patients was judged in the following manner. The patients of specimens judged to be a low risk by both of the conventional method 2 and the pathological diagnostic items were judged as the Low group. The patients of specimens judged to be a high risk by either the conventional method 2 or the pathological diagnostic items were judged as the High group.

The hazard ratios of each combination (Low group versus High group, Cox proportional hazard model) are shown in Table 5 below. Further, values obtained by dividing the hazard ratios of each combination by the sum of each hazard ratio of each item are shown in Table 5 and FIG. 5.

TABLE 5

| Term | HR | Sum of HR/HR |
|---|---|---|
| Conventional method 1 + age | 2.653 | 0.749 |
| Conventional method 1 + tumor diameter | 1.900 | 0.502 |
| Conventional method 1 + lymph node metastasis | 7.629 | 1.075 |
| Conventional method 1 + histological grade classification | 4.579 | 1.323 |
| Conventional method 1 + PR expression | 1.971 | 0.539 |
| Conventional method 1 + Her2 expression | 0.677 | 0.216 |
| Conventional method 2 + age | 1.622 | 0.537 |
| Conventional method 2 + tumor diameter | 1.637 | 0.501 |
| Conventional method 2 + lymph node metastasis | 1.707 | 0.260 |
| Conventional method 2 + histological grade classification | 1.140 | 0.388 |
| Conventional method 2 + PR expression | 1.633 | 0.521 |
| Conventional method 2 + Her2 expression | 0.795 | 0.304 |
| Conventional method 1 + conventional method 2 (present invention) | 9.177 | 2.316 |

When the age, i.e., one of the pathological diagnostic items, and the conventional method 1 which are combined with reference to Table 5, the obtained hazard ratio was 2.653. This value was lower than a value "3.545" obtained by adding each hazard ratio shown in Table 4. Similarly, when other pathological diagnostic items were combined with the conventional method 1 or the conventional method 2, the obtained hazard ratio was lower than a value obtained by adding each hazard ratio or equal to the value.

Figure 5:
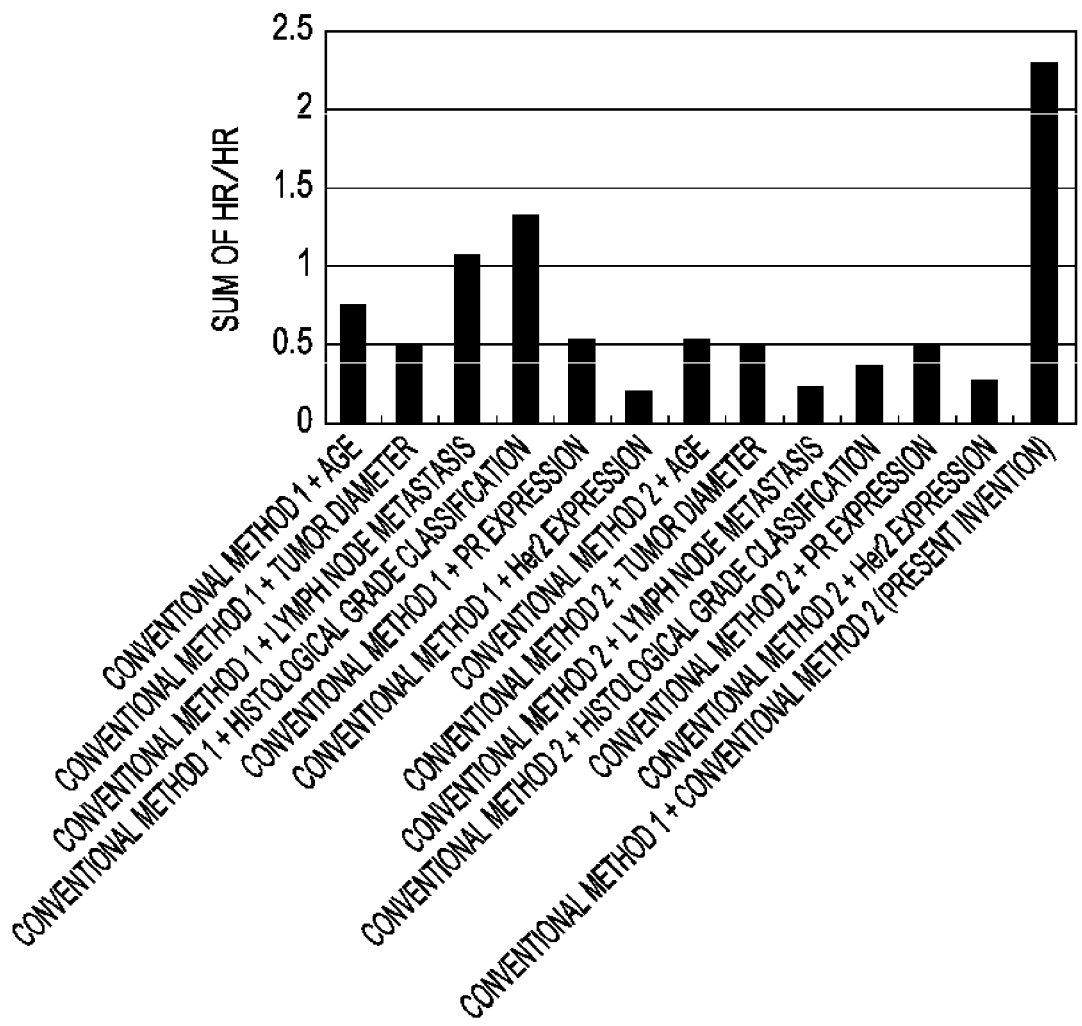
FIG. 5 is a graph showing a comparison of the judgment accuracies when the risk of recurrence is examined based on each combination of the expression levels and activity values of two types of CDKs and various pathological diagnostic items.

On the other hand, when the conventional method 1 and the conventional method 2, i.e., the judgment methods of the present invention, were combined, the obtained hazard ratio was 9.177. This value was significantly higher than a value "3.962" obtained by adding each hazard ratio shown in Table 4. FIG. 5 is a graph showing values obtained dividing the hazard ratio obtained by the combination of each item shown in Table 5 by the sum of the hazard ratios for each item for each combination.

The judgment accuracy of the judgment method of the present invention in which the conventional method 1 and the conventional method 2 were combined with reference to FIG. 5 was significantly improved as compared with other combinations of judgment methods.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is:

1. A method of judging a risk of cancer recurrence comprising a step of:
   acquiring an activity value and expression level of a first cyclin-dependent-kinase (CDK), an activity value and expression level of a second CDK, an expression level of urokinase plasminogen activator (uPA), and an expression level of plasminogen activator inhibitor 1 (PAI-1) from biological samples extracted from cancer patients;
   judging a risk of cancer recurrence using at least one processor based on the acquired activity value and expression level of the first CDK, the activity value and expression level of the second CDK, the expression level of uPA, and the expression level of PAI-1; and
   outputting instructions whether or not to perform an adjuvant therapy based on the judged risk of cancer recurrence,
   wherein a recurrence risk score of the cancer recurrence is a value acquired based on Equation (1):

$$\text{(Recurrence risk score)} = F(x) \times G(y) \tag{1}$$

(wherein x represents a first CDK specific activity, the first CDK specific activity is expressed by a first CDK activity value/first CDK expression level; y represents a specific activity ratio, the specific activity ratio is expressed by a second CDK specific activity/first CDK specific activity, and the second CDK specific activity is expressed by a second CDK activity value/second CDK expression level), and
   wherein the risk of cancer recurrence is judged as low when the recurrence risk score is less than a first threshold, the expression level of uPA is less than a second threshold, and the expression level of PAI-1 is less than a third threshold in the judgment step.

2. The method according to claim 1, wherein the recurrence risk score is acquired based on the activity value and expression level of the first CDK and the activity value and expression level of the second CDK in the judging step and the risk of cancer recurrence is judged based on the acquired recurrence risk score, the expression level of uPA, and the expression level of PAI-1.

3. The method according to claim 1, wherein the F(x) and G(y) are Equations (2) and (3):

$$F(x) = a/(1 + \text{Exp}(-(x-b)xc)) \tag{2}$$

$$G(y) = d/(1 + \text{Exp}(-(y-e)xf)) \tag{3}$$

(wherein, a, b, and c are constants defined by a correlation between x and a cancer recurrence rate; and d, e, and f are constants defined by a correlation between y and a cancer recurrence rate).

4. The method according to claim 2, wherein the first CDK specific activity expressed by a first CDK activity value/first CDK expression level is further acquired and the risk of cancer recurrence is judged based on the acquired first CDK specific activity, the recurrence risk score, the expression level of uPA, and the expression level of PAI-1 in the judgment step.

5. The method according to claim 4, wherein the risk of cancer recurrence is judged as low when the recurrence risk score is less than the first threshold, the first CDK specific activity is less than the fourth threshold, the expression level of uPA is less than the second threshold, and the expression level of PAI-1 is less than the third threshold in the judgment step.

6. The method according to claim 1, wherein the first CDK is CDK1 and the second CDK is CDK2.

7. A non-transitory computer program product for enabling a computer to judge a risk of cancer recurrence comprising:
   a computer readable medium and software instructions, on the computer readable medium, for enabling the computer to perform prejudged operations comprising:
   acquiring an activity value and expression level of a first cyclin-dependent-kinase (CDK) acquired from biological samples extracted from cancer patients, an activity value and expression level of a second CDK, an expression level of urokinase plasminogen activator (uPA), and an expression level of plasminogen activator inhibitor 1 (PAI-1);
   judging the risk of cancer recurrence based on the acquired activity value and expression level of the first CDK, the activity value and expression level of the second CDK, the expression level of uPA, and the expression level of PAI-1; and
   outputting the acquired judgment results and instructions whether or not to perform an adjuvant therapy based on the acquired judgment results,
   wherein a recurrence risk score of the cancer recurrence is a value calculated based on Equation (1):

$$\text{(Recurrence risk score)} = F(x) \times G(y) \tag{1}$$

(wherein x represents a first CDK specific activity, the first CDK specific activity is expressed by a first CDK activity value/first CDK expression level; y represents a specific activity ratio, the specific activity ratio is expressed by a second CDK specific activity/first CDK specific activity, and the second CDK specific activity is expressed by a second CDK activity value/second CDK expression level), and
   wherein the risk of cancer recurrence is judged as low when the recurrence risk score is less than a first threshold, the expression level of uPA is less than a second threshold, and the expression level of PAI-1 is less than a third threshold in the judgment operation.

8. The computer program product according to claim 7, wherein the judgment operation calculates the recurrence risk score based on the activity value and expression level of the first CDK and the activity value and expression level of the second CDK which are received by the receiving operation and judges the risk of cancer recurrence based on the calculated recurrence risk score, the expression level of uPA, and the expression level of PAI-1.

9. The computer program product according to claim 7, wherein the F(x) and G (y) are Equations (2) and (3):

$$F(x) = a/(1 + \text{Exp}(-(x-b)xc)) \tag{2}$$

$$G(y) = d/(1 + \text{Exp}(-(y-e)xf)) \tag{3}$$

(wherein, a, b, and c are constants defined by a correlation between x and a cancer recurrence rate; and d, e, and f are constants defined by a correlation between y and a cancer recurrence rate).

10. The computer program product according to claim 8, wherein the judgment operation calculates the first CDK specific activity expressed by the first CDK activity value/first CDK expression level and judges the risk of cancer recurrence based on the calculated first CDK specific activity, the recurrence risk score, the expression level of uPA, and the expression level of PAI-1.

11. The computer program product according to claim 10, wherein the judgment operation judges the risk of cancer recurrence as low when the recurrence risk score is less than the first threshold, the expression level of uPA is less than the second threshold, the expression level of PAI-1 is less than the third threshold, and the first CDK specific activity is less than the fourth threshold.

12. The computer program product according to claim 7, wherein the first CDK is CDK1 and the second CDK is CDK2.

13. The computer program product according to claim 8, wherein the risk of cancer recurrence is judged as high when the recurrence risk score is higher than the first threshold, the expression level of uPA is higher than the second threshold, or the expression level of PAI-1 is higher than the third threshold in the judgment operation.

14. The computer program product according to claim 10, wherein the risk of cancer recurrence is judged as high when the recurrence risk score is higher than the first threshold, the expression level of uPA is higher than the second threshold, the expression level of PAI-1 is higher than the third threshold, or the first CDK specific activity is higher than the fourth threshold in the judgment operation.

15. The computer program product according to claim 8, wherein the biological samples extracted from cancer patients are mammary tissues.

* * * * *